(12) United States Patent
Vidaud et al.

(10) Patent No.: US 6,541,246 B2
(45) Date of Patent: Apr. 1, 2003

(54) METHOD FOR DETECTING AND FOR QUANTIFYING ADENOVIRUSES

(75) Inventors: Michel Vidaud, Fontenay Sous Bois (FR); Eric Gautier, Paris (FR); Patrick Saulnier, Chatenay-Malabry (FR)

(73) Assignee: Gencell S.A., Vitry sur Seine (FR)

( * ) Notice: Subject to any disclaimer, the term of this patent is extended or adjusted under 35 U.S.C. 154(b) by 0 days.

(21) Appl. No.: 09/778,898

(22) Filed: Feb. 8, 2001

(65) Prior Publication Data

US 2002/0061516 A1 May 23, 2002

Related U.S. Application Data

(60) Provisional application No. 60/227,912, filed on Aug. 28, 2000.

(30) Foreign Application Priority Data

Feb. 8, 2000 (FR) .............................................. 00 01554

(51) Int. Cl.[7] .............................. C12Q 1/70; C12Q 1/68; C12Q 1/06; C12N 15/00; C07H 21/04
(52) U.S. Cl. ........................... 435/320.1; 435/5; 435/6; 435/39; 536/24.3; 536/23.1
(58) Field of Search ....................... 435/5, 6, 39, 320.1; 536/24.3, 23.1

(56) References Cited

FOREIGN PATENT DOCUMENTS

| | | |
|---|---|---|
| DE | 197 16 456 A1 | 10/1998 |
| DE | 198 16 902 A1 | 10/1999 |
| JP | 07327700 | 12/1995 |

OTHER PUBLICATIONS

Allard, A., et al., " Detection of Adenoviruses in Stools From Healthy Persons and Patients with Diarrhea by Two–Step Polymerase Chain Reaction," *J. of Medical Virology*, 37:149–157, (1992).

Allard, A., el al., " Polymerase Chain Reaction for Detection of Adenoviruses in Stool Samples," *J. of Clinical Microbiology*, 28:2659–2667, (1990).

Li, Q.–G., et al., "Hydropathic Characteristics of Adenovirus Hexons," *Arch. Virol.*, 142:1307–1322, (1997).

Poddar, S.K., "Symmetric vs Asymmetric PCR and Molecular Beacon Probe in the Detection of a Target Gene of Adenovirus," *Molecular and Cellular Probes*, 14:25–32, (2000).

Takeuchi S., et al., "Serotyping of Adenoviruses on Conjunctival Scrapings by PCR and Sequence Analysis," *J. of Clinical Microbiology*, 37:1839–1845, (1999).

*Primary Examiner*—Hankyel T. Park
(74) *Attorney, Agent, or Firm*—Finnegan, Henderson, Farabow, Garrett & Dunner, L.L.P.

(57) ABSTRACT

Method for detecting and for quantifying adenoviruses by polymerase chain reaction (PCR). The method makes it possible to detect, in a single reaction, the various adenovirus serotypes and to quantify very low amounts.

53 Claims, 1 Drawing Sheet

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
ycccatggay gagcccacmc t                                            21

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
gagaasggbg tgcgcaggta sac                                          23

<210> SEQ ID NO 3
<211> LENGTH: 26
<212> TYPE: DNA

<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3
caccagccac accgcggcgt catcga                                         26

<210> SEQ ID NO 4
<211> LENGTH: 1001
<212> TYPE: DNA
<213> ORGANISM: Adenovirus

<400> SEQUENCE: 4
aggtggccat tacctttgac tcttctgtca gctggcctgg caatgaccgc ctgcttaccc    60
ccaacgagtt tgaaattaag cgctcagttg acggggaggg ttacaacgtt gcccagtgta   120
acatgaccaa agactggttc ctggtacaaa tgctagctaa ctacaacatt ggctaccagg   180
gcttctatat cccagagagc tacaaggacc gcatgtactc cttctttaga aacttccagc   240
ccatgagccg tcaggtggtg gatgatacta aatacaagga ctaccaacag gtgggcatcc   300
tacaccaaca caacaactct ggatttgttg gctaccttgc ccccaccatg cgcgaaggac   360
aggcctaccc tgctaacttc ccctatccgc ttataggcaa gaccgcagtt gacagcatta   420
cccagaaaaa gtttctttgc gatcgcaccc ttttggcgcat cccattctcc agtaacttta   480
tgtccatggg cgcactcaca gacctgggcc aaaaccttct ctacgccaac tccgcccacg   540
cgctagacat gacttttgag gtggatccca tggacgagcc caccttctt tatgttttgt   600 ttgaagtctt tgacgtggtc cgtgtgcacc ggccgcaccg cggcgtcatc gaaaccgtgt   660
acctgcgcac gcccttctcg gccggcaacg ccacaacata agaagcaag caacatcaac    720 aacagctgcc gccatgggct ccagtgagca ggaactgaaa gccattgtca agatcttgg    780 ttgtgggcca tattttttgg gcacctatga caagcgcttt ccaggctttg tttctccaca   840
caagctcgcc tgcgccatag tcaatacggc cggtcgcgag actggggcg tacactggat    900 ggcctttgcc tggaacccgc actcaaaaac atgctacctc tttgagcct ttggcttttc    960 tgaccagcga ctcaagcagg tttaccagtt tgagtacgag t                     1001

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
ycccatggay gagcccacmc t                                              21

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
gagaasggbg tgcgcaggta sac                                            23

METHOD FOR DETECTING AND FOR QUANTIFYING ADENOVIRUSES

This application claims the benefit of provisional application 60/227,912 filed Aug. 28, 2000.

The present invention relates to a method for detecting and for quantifying, in diverse biological media, adenovirus nucleic acids by real-time polymerase chain reaction (PCR) measurement. A subject of the invention is also oligonucleotides for carrying out this method.

BACKGROUND OF INVENTION

Gene therapy is currently undergoing considerable development. Adenoviruses, which are naturally responsible for generally benign infections, are among the vectors used because of their many advantages.

The extension of the clinical development of these adenoviral vectors to late phases II and III for the purposes of registration and of authorization for marketing makes it necessary to develop, validate and implement specific and sensitive techniques which allow the measurement of the quantitative and qualitative biodistribution of adenovectors in diverse biological compartments, and the detection of the emergence, at low viral load, of infection with contaminants from the production of adenovectors (in particular replication-competent recombinant adenovectors). It is also necessary to detect intercurrent adenoviral infections which are due to wild-type viruses of various serotypes, which are responsible for the vast majority of the incidence of these natural infections, whether these infections are clinically florid or latent, and to determine the virological kinetics of these wild-type infections and the clinical significance in diverse situations, in the general population or in patients who are at risk (patients suffering from cancer, transplant patients, immunosuppressed or immunodepressed patients, etc.).

The presence of an adenovirus in permissive cell culture is visualized, in the detection techniques routinely used to date, by a cytopathic effect in the cell layer. In order to demonstrate that this cytopathic effect is indeed due to an adenovirus, an antigen which is specific for the adenovirus is detected by the ELISA method.

Techniques for amplifying extracted nucleic acids of adenoviruses by PCR have also been described. Thus, Japanese patent application JP 07327700 describes a PCR-type method in which portions of the DNA encoding hexon, which is an adenovirus capsid protein, are amplified. The amplification products are "dot-blotted", then hybridized with probes which are specific for each serotype. This method is thus intended to identify the subgroups and serotypes, and not to detect and quantify all of the adenoviruses present in a sample. In addition, the sensitivity of this method is low and thus generally unsuitable for precise measurements, such as those required during the monitoring of patients treated by gene therapy.

Pring-Akerblom et al. (Journal of Medical Virology, 58:87–92, (1999), have also described a method which uses six pairs of primers in the same PCR reaction (so-called multiplex PCR). The identification of the subgroup is carried out by loading the PCR products onto electrophoresis gel and then determining the size of the PCR products.

Crawford-Miksza et al. (Journal of Clinical Microbiology, 37:1107–1112, (1999), have described a hexon PCR which specifically detects type 4, 7 and 21 adenoviruses using consensus primers comprising inosine as the nucleic base in the event of mismatching in certain variable position. In that document, nine distinct primers are described.

These prior techniques use a standard PCR and a conventional analysis method which is generally on electrophoresis gel with or without hybridization.

None of these techniques make it possible both to broadly detect adenoviruses originating from the majority of the known serotypes, and to quantify the viral loads thereof with a sensitivity which is suitable for the needs of gene therapy in particular.

The aim of the present invention is thus to resolve these problems by providing a technique which is sensitive and which makes it possible to detect the majority of the adenovirus serotypes.

The applicants have surprisingly shown that such advantages are obtained by amplifying in real time a given sequence of the DNA encoding hexon with the aid of primers having limited degeneracy, and revealing the amplification product with the aid of a nondegenerate probe.

SUMMARY OF THE INVENTION

The present invention first of all relates to a method for detecting and/or for quantifying adenovirus nucleic acids in a biological sample wherein:

an adenovirus nucleotide sequence is amplified by real-time PCR using degenerate sense primers and degenerate antisense primers, wherein said primers are chosen from oligonucleotides having at least 80% homology with a sequence between nucleotides 21000 and 22000 of type 5 adenovirus sequence, and which corresponds to sequence SEQ ID No. 4, and oligonucleotides comprising a complementary sequence thereof, and an amplification reaction product may be detected using a nondegenerate probe comprising an oligonucleotide having at least 80% homology with a sequence between nucleotides 21000 and 22000 of type 5 adenovirus sequence, which corresponds to sequence SEQ ID No. 4, and oligonucleotides comprising a complementary sequence thereof, wherein said product may be detected during a number of amplification reaction cycles which is sufficient to allow the production of a measurable amount of amplification product.

The term "real-time PCR" is intended to mean any amplification technique which makes it possible to monitor the evolution of an ongoing amplification reaction. Polymerase Chain Reaction is abbreviated as "PCR".

Generally, sequences of the primers and/or of the probe may comprise at least 80% homology with at least one sequence between nucleotides 540 and 780 of sequence SEQ ID No. 4, or with a complementary sequence thereof. The two primers are chosen on the sense and antisense strands, respectively, and in such a way as to allow the amplification of a DNA fragment. With regard to the probe, it is chosen so as to hybridize with the DNA fragment resulting from the amplification. The PCR primers in accordance with the present invention which are used to amplify the target adenovirus nucleic acid in a sample are located in a region which is constant for the hexon gene of human adenoviruses, and the hybridization site of the probe in accordance with the present invention is located between the two primers. In one embodiment, the adenoviruses are of human tropism.

Generally, said oligonucleotides may comprise at least 15 nucleotides, and the probe has a theoretical melting temperature Tm which is higher than the theoretical Tm of the primers by approximately $10°$ C.$\pm 0.5$.

A method of the invention is termed hexon PCR method in abbreviated form in the remainder of the text. It comprises a repetition of a cycle comprising:

separation of the strands to be amplified by heating the DNA extracted from the sample, hybridization of the probe, hybridization with primers as defined above, and elongation with a polymerase.

In one embodiment, the amplification method comprises the sense and antisense primers HEX1 and HEX2 described below. In a further embodiment, the amplification product is hybridized with the HEX probe described below.

One subject of the present invention is an oligonucleotide, comprising at least 10 consecutive nucleotides of the following sequence SEQ ID No. 1 or of a sequence having at least 80% sequence homology with said sequence:

5'-YCC CAT GGA YGA GCC CAC MCT-3' in which Y represents C or T, and M represents A or C. In one embodiment of the invention, said oligonucleotide has at least 90% sequence homology with said sequence. In another embodiment, said oligonucleotide has at least 95% sequence homology with said sequence.

In yet another embodiment, said oligonucleotide comprises between 15 and 30 nucleotides.

One subject of the present invention is a HEX1 sense primer comprising a mixture of oligonucleotides which satisfy this definition. The HEX1 primer has three degeneracies at positions 1, 10 and 19 which make it possible to cover the majority of the serotypes.

Another subject of the present invention is a second oligonucleotide, comprising at least 10 consecutive nucleotides of the following sequence SEQ ID No. 2 or of a sequence which shows at least 80% sequence homology with said sequence:

5'-GAG AAS GGB GTG CGC AGG TAS-3' in which S represents G or C, and B represents C, G or T. In one embodiment of the invention, said second oligonucleotide has at least 90% sequence homology with said sequence. In another embodiment, said second oligonucleotide has at least 95% sequence homology with said sequence.

In yet another embodiment, said second oligonucleotide comprises between 15 and 30 nucleotides.

Another subject of the present invention is a HEX2 antisense primer comprising a mixture of oligonucleotides which satisfy this definition. The HEX2 primer has three degeneracies at positions 6, 9 and 21 which make it possible to cover the majority of the serotypes sequenced.

In one embodiment of the invention said primers comprise at least two oligonucleotides. In other embodiments, said primers may comprise three or four oligonucleotides.

The positions of the sequences SEQ ID No. 1 and 2, which are located in the 3' portion of the Open Reading Frame ("ORF") encoding the Hexon protein, are, talking the complete sequence of the type 5 adenovirus (filing No. M73260) as reference, 21565 (HEX1) and 21656 (HEX2), respectively. They correspond to positions 21048 and 21139 of the Ad5CMVp53 sequence (length 35308 bp).

The applicants have shown that primer concentration is a parameter of real-time PCR. Therefore, the degeneracy of the HEX1 and HEX2 primers was limited.

A subject of the present invention is also a third oligonucleotide, comprising at least 10 consecutive nucleotides of the following sequence SEQ ID No. 3 or of a sequence having at least 80% sequence homology with said sequence, or with a sequence complementary to said sequence:

5'-CAC CAG CCA CAC CGC GGC GTC ATC GA-3'.

In one embodiment of the invention, said third oligonucleotide has at least 90% sequence homology with said sequence. In another embodiment, said third oligonucleotide has at least 95% sequence homology with said sequence.

In yet another embodiment, said third oligonucleotide comprises between 20 and 35 nucleotides.

A subject of the present invention is also a HEX probe comprising an oligonucleotide having this sequence.

It also relates to oligonucleotides having a sequence complementary to those of the oligonucleotides mentioned above.

In one embodiment of the present invention, the probe comprises a revealing molecule or revealing system of molecules. Said revealing system may comprise a reporter dye and a quenching dye, which are bound to the 5' and 3' ends, respectively, of the probe. In one embodiment, said reporter dye is a fluorescent dye and said quenching dye is a fluorescence-quenching dye. According to another embodiment, the revealing system consists of a reporter/quencher pair 6-carboxyfluorescein (FAM) and 6-carboxytetramethyl-rhodamine (TAMRA) bound in the 5' and 3' positions, respectively, of the probe. In yet another embodiment, one of the primers is labeled in this way with a reporter/quencher pair and said primer then performs the role of a probe.

In one embodiment of the invention, the probe is:

5'FAM-CAC CAG CCA CAC CGA GGC GTC ATC GA-TAMRA 3'

Said revealing system can also optionally be a so-called tailing revealing system. Wherein said tailing revealing system comprises at one of the ends of the probe, a tail which can self-pair. This self-pairing is detected with the aid of a label which binds specifically to the sequence in this configuration. In the presence of a target, unpairing takes place and a signal is given off. In the absence of a target, the signal is not given off. Other revealing systems can also be used. In another revealing system, detection may involve hybridization of probe to said amplification product and a signal is given off.

As a variation, the sense and antisense primers can comprise a revealing molecule or revealing system of molecules.

The PCR product obtained by the method which is the subject of the present invention, using the primers of sequences SEQ ID No. 1 and SEQ ID No. 2, may generally be 114 bp and may have a GC% of approximately 58.8%.

The polymerase used in the present invention may be any enzyme which has polymerase activity and which can be used under the PCR operating conditions. In one embodiment, the polymerase is Taq polymerase.

A subject of the present invention is also a kit of reagents for real-time PCR-type amplification reaction for detecting adenoviruses, comprising a pair of sense and antisense primers and a probe as described above. Said kit may also comprise negative controls and/or positive controls, such as, for example, two negative controls and two positive controls. Said kit may comprise at least one separate compartment, wherein each compartment may comprise at least one of said primers or probe. Said kit may comprise two or more compartments.

A subject of the present invention is also a PCR method for detecting and/or quantifying adenoviruses in a sample to be measured which is likely to contain them, comprising a real-time PCR which uses a kit according to the invention.

According to one embodiment of the invention, said two positive controls are extracted in parallel to a series of samples to be assayed, and comprise a standard comprising a purified and titered adenovirus solution and a calibrator which is suitable for the type of sample to be measured.

The method in accordance with the invention may be applicable to detecting and/or quantifying adenoviruses present in samples such as culture suspension or supernatant, plasma, urine, oropharyngeal washes, lymphocytes, seminal fluids, tumor or nontumor biopsies, rectal swabs, feces or ascites.

The present invention also relates to a method for selecting adenoviruses which are useful as vector candidates by evaluating the replication performances of the adenoviruses using a detection and/or quantification method according to the invention to monitor adenoviral multiplication kinetics.

The present invention also relates to a method for diagnosing the serotype of adenoviruses present in a sample to be tested, comprising implementing a method of the invention, and then in sequencing the PCR product obtained.

The nucleotide sequences of the various serotypes encoding the Hexon protein were obtained from publicly-available databanks, or were sequenced by conventional methods. The Ad3, Ad7, Ad12, Ad14, Ad16 and Ad21 serotypes have an A residue at position 9 of the HEX probe. The Ad5, Ad1, Ad2, Ad6, Ad13, Ad40 and Ad48 serotypes have a G residue at this same position, whereas the Ad4 and Ad41 serotypes have a C residue. The sequence which has an A residue was chosen, since the G-type sequence, unlike the A-type or C-type sequences, has a very highly stable secondary structure (DG=−7.1 kcal/mol) which is likely to disturb its hybridization and/or its displacement and/or its degradation during polymerization. On the other hand, the A-type sequence is more common than the C-type sequence.

The A/C (Ad5CMVp53 and 5,1, 2, 6, 13, 40 and 48 serotypes) or A/G (4 and 41 serotypes) mismatches cause a decrease in the delta Rn without significant modification of the Ct (delta Rn is the difference in fluorescence detected between the measured fluorescence of the background noise and the detected fluorescence of the sample to be tested; Ct is defined as the number of fractional cycles in which the fluorescence generated by cleaving the probe significantly exceeds, in general by 10-fold, the background noise).

Ad5, Ad4, Ad12 and Ad14 serotypes and Ad5CMVp53 have additional differences at position 5 for the Ad5 serotype and Ad5CMVp53

24 for the Ad4 and Ad12 serotypes 3, 12 and 19 for the Ad14 serotype

Despite these differences, it is possible, surprisingly, to detect the nucleotide sequences encoding the hexon proteins of these serotypes.

One of the advantages of the present method for detecting and/or for quantifying human adenoviruses, with respect to the methods described in the prior art, is an outstanding detection sensitivity with a detection threshold of 10 particles or 1 pfu (plaque forming unit) by PCR reaction.

Another advantage lies in the universality of the method, since it has been possible to detect and quantify 17 different serotypes of human adenoviruses, which are representative of all of the subgroups A to F.

In addition, the analysis of the PCR products is carried out directly at the end of the PCR cycles by reading the fluorescence obtained during the cycles. It is not therefore necessary to work with PCR products which are at risk of being contaminated for the subsequent analyses.

Furthermore, the raw data may be completely recorded and preserved. Specifically, each PCR analysis may be stored as computer files which can be archived for a long period of time without alteration. The raw data can be re-analyzed at any moment, permitting re-analysis if criteria change. Conserving of the raw data is essential when it is necessary to meet the standards of Good Laboratory Practice.

In addition, the quantification of the number of targets placed in the reaction at the start is generally very reliable and reproducible. The detection of the PCR product is carried out during the PCR cycles, often with the aid of a fluorescent probe or other reporter system. This is necessary to detect the PCR product, and generally takes place in the middle of the exponential phase of PCR, and not at the end point; this detection principle is thus more sensitive and more specific.

Another advantage lies in the fact that nonspecific amplifications are avoided due to the hot start principle, the real-time PCR being carried out in the presence of a heat-stable DNA polymerase which is activated at the first denaturation.

In implementing the present invention, reference may optionally be made to a general review of PCR techniques, and to the explanatory note entitled "Quantitation of DNA/RNA Using Real-Time PCR Detection" published by Perkin Elmer Applied Biosystems (1999) and to PCR Protocols (Academic Press New York, 1989).

DETAILED DESCRIPTION OF THE INVENTION

Materials and Methods

Figure 1:
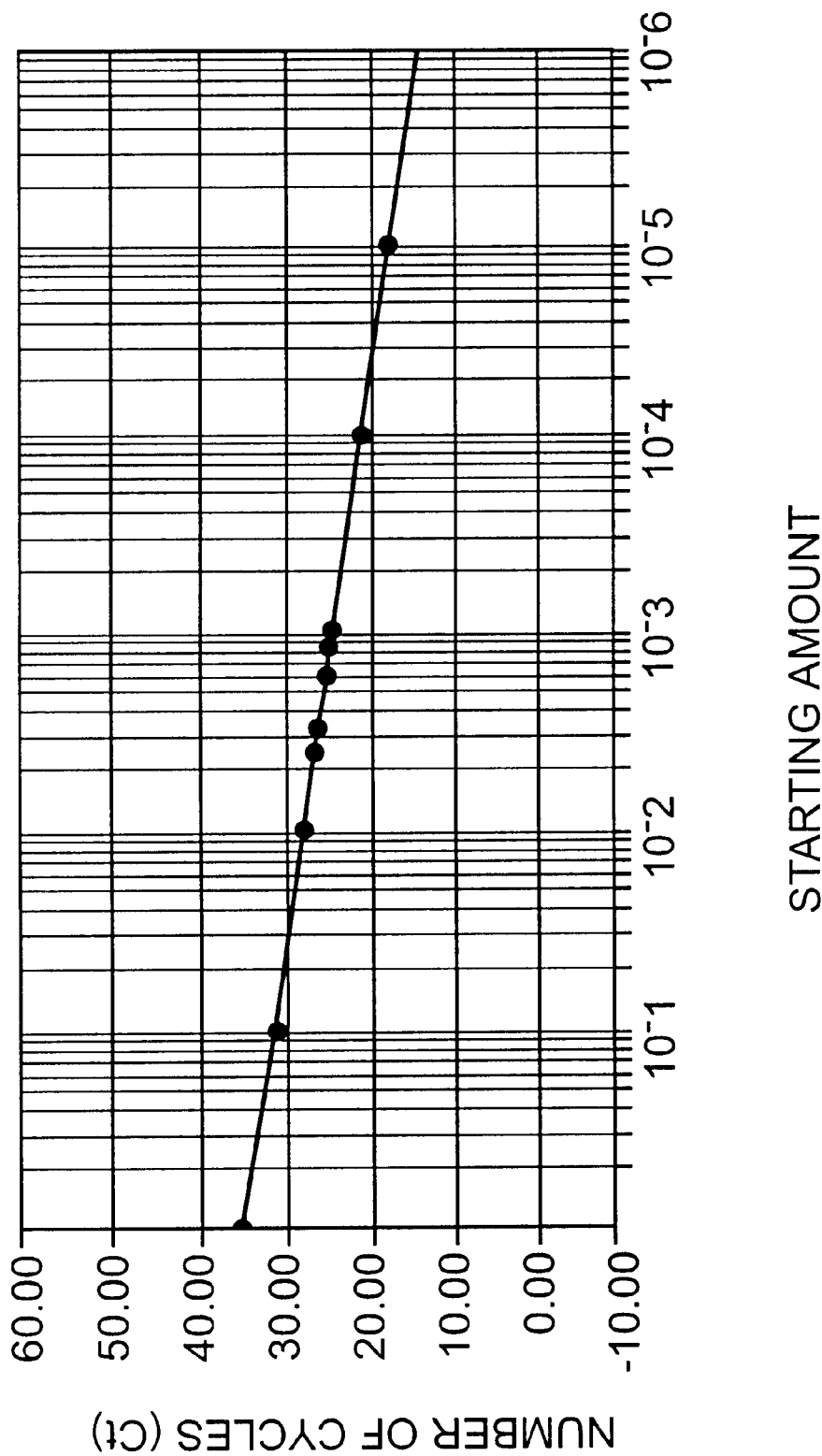
FIG. 1 is a standard curve generated by PCR showing number of cycles versus quantity of starting material.

Adenovirus, Culture Supernatant and Cell Line Collection

The culture supernatants of various human adenovirus serotypes originated from the laboratory of Prof. Freymuth (Virology Department, University Teaching Hospital, Caen) or the Centre de reference IGR/RPR Gencell (France).

Certain titered wild-type adenoviruses (Ad2 and Ad5) originated from the Mixed Research Unit No. 1592 (Emmanuelle Vigne, Vectorology and Gene Transfer Unit, Gustave-Roussy Institute).

The titered Ad5CMVp53 originated from the Production Unit of RPR Gencell, Vitry (Didier Faucher). The titers were provided as number of pfu (plaque forming units). This unit was the unit of reference for quantification.

The 293 cell line originated from ATCC (CRL 1573).

The A549 cell line (ATCC: CCL 185) was kindly provided by E. Vigne and A. Fallourd, RPR Gencell.

The MRC5 cell line originated from bioMerieux (ref. 84002, France).

Clinical Samples:

The clinical samples (plasma, urine, oropharyngeal washes, feces) originated either from healthy volunteers or from patients hospitalized at the Gustave-Roussy Institute.

Certain plasmas originated from the Transfusion Center, either by buying a bag originating from approximately 200 donors, or bags which can no longer be used for a medical purpose.

Storage Conditions

The adenovirus collections and the clinical samples were transported in dry ice and, as soon as they were received, stored at −80° C.

The various stages of reception, aliquoting and analysis necessitated a certain number of freezing and thawing cycles (adenoviruses or clinical samples). In order to be under the same conditions, the controls (standard and calibrators) underwent the same number of freezing and thawing cycles as the clinical samples diagnosed.

Controls and Standard

There were two types of negative control:

A PCR negative control or NTC (non template control) which consisted of the PCR buffer with distilled water (without target). The Ct value should have been 50, since 50 PCR cycles were carried out.

The second type of negative control was the extraction negative control which was introduced from the extraction step. In general, it consisted of 200 µl of physiological saline, and it was extracted in parallel with a series of extractions (in general 1 for 10). The Ct value should also have been 50.

There were two types of positive "controls":

The standard, which consisted of a purified and titered ($\approx 5 \times 10^5$ pfu) adenovirus solution, was extracted in parallel to a series of samples to be assayed. The nucleic acid extract was diluted (in general 10-fold serial dilutions) so as to constitute the various standard points for the construction of the standard curve (Figure).

The second type of positive control was the calibrator. Various types of calibrator exist, depending on the type of sample to be diagnosed. It consisted of 200 µl of medium which was closest to the sample, and of a known amount of adenovirus which was in the middle of the standard range (in general $5 \times 10^3$ pfu). The media used for manufacturing the calibrators were physiological saline for the oropharyngeal washes of a pool of plasma from 200 healthy donors for the plasmas, of urine from healthy individuals for the urines and fresh culture medium for the culture supernatants. These calibrators verified that the extraction technique was correct. The quantification value with respect to the expected theoretical value made it possible, by simple rule of three, to readjust the final quantification obtained with the samples to be tested.

Machine and quantification

All the PCR reactions were carried out with the aid of the ABI Prism 7700 machine (Perkin-Elmer Applied Biosystem), which machine detected the signal with the aid of a fluorescent probe (TaqMan™ probe) during the PCR cycles.

The 7700 system is a thermocycler, in which each well (n=96) was connected to an optical fiber, this optical fiber was connected to a laser. A CDD camera collected the fluorescent emissions about every 6 seconds for each well. The S.D.S. (Sequence Detector System™) software analyzed the fluorescent data and determined the number of target copies in a sample.

The quantification was based on the principle of real-time PCR. Specifically, the PCR product was characterized during the PCR cycle at the moment at which the amplification was detectable by the degradation of the probe which was linked to the accumulation of PCR products. The higher the number of starting target copies, the fewer PCR cycles that were required in order to detect a significant increase in fluorescence.

The number of target copies in a sample was quantified by measuring the Ct value, and using a standard curve (Figure). In theory, if the PCR functions at 100%, 3.22 PCR cycles (Ct) were required in order to multiply the number of targets by 10. In general, a factor of 10 in the number of targets gave a difference in Ct values of between 3.4 to 3.6.

The second parameter (Delta Rn) was used to confirm that the PCR signal was positive. The delta Rn was the difference in fluorescence detected between the measured fluorescence of the background noise (in general measured between cycle 3 and cycle 15 of the PCR over the entire plate) and the detected fluorescence of the sample to be analyzed.

The present invention is illustrated by nonlimiting examples, and with reference to the attached figure which represents a standard curve of a hexon PCR method in accordance with the invention.

EXAMPLES

Example 1

Detection of Adenoviruses Originating from a Urine Sample 1.1. Preparation of the urine sample to be tested.

All the reagents used for this preparation originated from the kit which was named High Pure RNA Isolation Kit, and which was sold by Boehringer/Roche.

The sample was prepared as follows:

400 µl of lysis buffer was added to 200 µl of urine which had been preheated for 10 min at 370° C., and 400 µl of lysis buffer was added to each of the 200 µl controls.

Each sample was vortexed immediately and then incubated for 15 min at room temperature.

Placed each column on a 2.0 ml tube, and loaded the whole preparation at the center of the column. Centrifuged for 1 min at 8000 revs/min (Eppendorf 5417R) at 20° C.

Placed the column on a second 2.0 ml tube.

Added 500 µl of washing buffer II and then centrifuged for 1 min at 8000 revs/min (Eppendorf 5417R) at 20° C.

Placed the column on a third 2.0 ml tube.

Added 500 µl of washing buffer II and then centrifuged for 1 min at 8000 revs/min (Eppendorf 5417R) at 200° C.

Placed the column on a fourth 2.0 ml tube.

Added 200 µl of washing buffer II and then centrifuged for 3 min at 14,000 revs/min (Eppendorf 5417R) at 20° C.

Placed the column on a 1.5 ml Eppendorf tube (fifth tube) and identified the Eppendorf tube which collected the final eluate of nucleic acid extraction.

Added 50 µl of preheated distilled water.

Incubated for 3 min at 700° C. (dry bath).

Centrifuged for 1 min at 8000 revs/min (Eppendorf 5417R) at 20° C.

The nucleic acid extracts were conserved at 4° C. until the PCR step.

The "controls" and "standard" were prepared as described above ("materials and methods" section).

For the preparation of other types of sample, refer to Table No. 1 which illustrates the optimized extraction techniques for the detection of adenoviruses originating from various types of sample, including that of the present example.

1.2. Conditions for detection according to the hexon PCR method in accordance with the invention The concentrations of all of the reagents used in the amplification reactions, in particular the concentrations of "HEX1" sense and "HEX2" antisense primers, of "HEX" probe, and of $MgCl_2$ and other reagents of the TaqMan™ PCR Core Reagents Kit (Perkin-Elmer Applied Biosystems), are given in Table 2.

1.3. Results

The standard curve of a PCR detection method in accordance with the invention is represented in FIG. 1.

Example 2

Specificity of the Method in Accordance with the Invention

One of the applications of the hexon PCR method according to the invention was the detection of adenoviruses in culture supernatants.

According to the techniques of the prior art, the presence of an adenovirus in cell culture (permissive) was conventionally visualized by a cytopathic effect in the cell layer. In order to demonstrate that this cytopathic effect was indeed due to an adenovirus, an antigen which is specific for the adenovirus was detected (by ELISA, ex. Ref. K6021, Dako Diagnostic Ltd., Denmark House, England).

Nucleic acid extracts originating from the principal cell lines (Hep2, MRC5, 293 and A549, described above in the "materials and methods" section) used for the cellular diagnosis of human adenoviruses were tested in order to verify the negativity in hexon PCR according to the present invention. All the DNA extracts evaluated were negative, demonstrating the specificity of detection.

For the hexon PCR method of the invention, we demonstrated the "universal" nature of the detection with various human adenovirus serotypes.

17 different serotypes were evaluated (Table No. 3), and all the subgroups (A, B1, B2, C, D, E and F)were represented.

The collection of 17 serotypes was tested on two cell lines, MRC5 (Ref. 84002, bioMérieux, France) and A549 (ATCC: CCL 185), giving similar results. The results obtained on A549 are presented in Table 3. It was seen that the Ct values were similar except for the 12, 18 and 40 serotypes. These 3 serotypes corresponded to the adenoviruses which have the lowest titers. However, this large difference in Ct was generally due to the choice of TaqMan™ probe and primers in accordance with the present invention. Specifically, Ad12 exhibited two mismatches for the HEX1 sense primer of the invention and one mismatch for the HEX probe of the invention. Similarly, Ad40 exhibited one uncoupling for the HEX2 antisense primer of the invention and one uncoupling for the HEX probe of the invention. The sequence of the hexon gene for the 18 serotype was not available. It is probable that these results obtained with Ad18 were also due to mismatches.

It should be noted that, despite these uncouplings (two or three) of nucleotide sequences, the culture supernatants remain largely positive.

These results entirely confirm the "universal" nature of the hexon PCR because the 17 serotypes tested were representative of the 51 known serotypes.

Example 3

Sensitivity of the Method in Accordance with the Invention 3.1. Estimation of the detection threshold in number of particles.

Table 3 presents the results of the 17 adenovirus serotypes with Ct values obtained as a function of the number of particles per ml measured by the HPLC technique. With the exception of the 3 serotypes which had low titers (Ad12, Ad18 and Ad40), the Ct values were within a range of 8.1 to 9.1 for a number of particles of 1.1 to $8.5 \times 10^{10}$/ml.

If it is considered that the Ct value for the positivity limit is in the region of 40, and a difference of 3.5 Ct is taken for a factor of 10 in the number of targets, this represents a possible difference in the Ct value of 31 units. This difference represents approximately 9 base-10 logarithms. Consequently, depending on the serotypes, the detection threshold can be estimated as from 10 to 80 particles per PCR reaction.

3.2. Result of 101 standard ranges.

Over a period of 18 months, 101 standard ranges were tested using 101 independent extractions of a standard containing $5 \times 10^5$ pfu of Ad5CMVp53 in 200 µl. The final elution volume was 50 µl. 10 µl of extract of this standard with a 10-fold serial dilution range (pure, $10^{-1}$, $10^{-2}$, $10^{-3}$, $10^{-4}$ and $10^{-5}$) were analyzed in order to construct a standard range. The last dilution tested corresponds, in theory, to 1 pfu of Ad5CMVp53 in the PCR tube. All the range points were tested in duplicate by PCR (Ct1 and Ct2, Table 5).

The Ct values obtained with all the points containing 1 pfu of Ad5CMVp53 are presented in Table 5. Out of 202 PCR reactions, 8 reactions were negative (Ct=50), which represents only 4%. In the great majority of cases, the amount of 1 pfu of Ad5CMVp53 was positive in hexon PCR.

These results clearly confirmed the good sensitivity of detection. Depending on the batches of manufacture of Ad5CMVp53, the 1 pfu equivalent corresponds to 10 to 40 viral particles (≈target), which confirms the detection threshold estimated with the aid of the collection of wild-type adenoviruses.

Example 4

Kinetics of Adenoviral Culture

Two experiments demonstrated that it was possible to follow the kinetics of adenoviral multiplication with the aid of the hexon PCR method of the invention. These two experiments used either Ad5 on the MRC5 line, or Ad2 on the A549 line (Table No. 4). The results obtained for the two experiments were similar.

25 cm² culture flasks of cells were infected with adenovirus dilutions of between $10^5$ and 1 pfu. The culture medium (5 ml) was removed, and the cells were infected with various virus concentrations under a volume of 2 ml for 2 hours (at 37° C.). After the two hours, the medium was changed. After infection, the culture flasks were sampled every day (day 0 to day 11): 250 µl for the ELISA assay (detection of Hexon antigen) and 200 µl for the PCR detection according to the invention. 450 µl of fresh medium were reintroduced into the culture flask.

The CPE (cytopathic effect) (Table No. 4) appears between 4 days, for the $10^5$ point, and 8 days, for the 10 pfu point. A relationship exists between the amount of virus inoculated in the culture flask and the delay in positivity. The positivity threshold was 10 pfu/culture flask.

The appearance of the CPE was simultaneous with that of the Hexon antigen (ELISA assay). The positivity of the ELISA did not precede that of the CPE for any of the dilutions studied.

For the hexon PCR (Table No. 4), the Ct values for the negative controls (T) were slightly positive (37.6 to 37.8). This result may be explained either by a slight contamination by aerosols at the moment of inoculation of the culture flasks, or by a slight contamination at the moment of extraction. The first hypothesis was more probable, since, at day 10, the Ct values changed to 31.2 (difference of 6.5 Ct), which represents a 100-fold increase in the number of adenovirus copies. The hexon PCR method of the invention showed the existence of viral multiplication (significant decrease in the Ct) in the absence of CPE and of detection of the hexon antigen.

Depending on the dilutions tested, the hexon PCR method of the invention demonstrated, in an entirely surprising manner, from 2 to 4 "waves" of viral multiplication. Clearly, these results demonstrated that the hexon PCR method of the invention became positive earlier than the hexon ELISA or CPE. Thus, the hexon PCR method in accordance with the present invention was a minimum of 10 times more sensitive than the conventional cell culture assays (10-day culture+ ELISA assay).

These results, which were at the very least unexpected, obtained with the hexon PCR method of the invention can be exploited in general to easily and quickly learn the time of a viral cycle and its level of amplification. The latter two parameters were used for evaluating the replication performances of a virus.

Consequently, the hexon PCR method according to the invention can advantageously contribute to the selection of vector candidates with a view to biotechnological applications, in particular in gene therapy and/or expression. In addition to gene therapy utilities, these results demonstrate the usefulness of the present invention for studying viral biology and viral replication processes. In one embodiment, a viral researcher may use the disclosed invention to quantify viral replication processes in a viral culture.

Example 5

Repeatability and Reproducibility of the Method According to the Invention

The results of the 101 standards evaluated by hexon PCR (Table No. 5) made it possible to determine both the repeatability (intra-assay repetition) and the reproducibility (inter-assay repetition). The mean of the Ct values for 1 pfu was 37.2±1.8. This level of variation was relatively low, especially since it was the result of the variation of two steps: extraction and hexon PCR.

For the Ct values for 10 pfu (not shown), the mean was 33.7±1.7. The level of variation was very similar, since the deviations obtained were very close. It may be noted that the difference in Ct between the two means obtained with 1 pfu and 10 pfu was 3.5 Ct. This difference effectively corresponds to a 10-fold difference in the number of targets.

Example 6

Clinical Samples

Clinical samples were tested with independent extractions and in different series of hexon PCR. The results of the hexon PCR (Ct values) of 8 plasmas and 20 urines are presented in Table No. 6.

In general, when the Ct values were lower than or equal to 36, the variations in Ct for the same nucleic acid extract (Ct1 and Ct2) rarely exceeded the value of 1 Ct (factor of 2 for the quantification). It was for this reason that all the samples with Ct values$\leq$to 36 were considered to be quantifiable (status "positive-quantifiable) and, between 36 and 43, the samples were considered to be positive but nonquantifiable (status positive-detectable).

For the plasmas (Table No. 6), within the same nucleic acid extract, there was rarely a difference of more than 1 Ct, except for extract No. 1 of plasma No. 3289, and extract No. 3 of plasma No. 3579. In the latter case, the value of 44.6 for Ct1 was aberrant. Of course, within the various nucleic acid extracts, the variation in Ct was more considerable, but rarely exceeds a value of 2 Ct (factor of 4 for the quantification)

For the urines (Table No. 6), within the same nucleic acid extract, there was no more than 1 Ct of deviation, except when the Ct values were greater than 36. Specifically, for Ct values greater than 36, the level of positivity was quite low, which explains a higher level of variation.

Within the various nucleic acid extracts, the variation in Ct was also more considerable, exceeding only rarely a value of 2 Ct between two different extracts, except for urine No. 2403, which has a difference of 3 Ct (factor of 8 in quantification). Of course, some urines (Nos. 2029, 2626, 3736, 3763, 3765 and 5399) have very high Ct values (in general>than 40), which demonstrates very low positivity. In the latter cases, it was understood that it was possible to easily go from a positive signal to a negative signal (Ct=50).

Overall, the results of the hexon PCR detection method in accordance with the invention on the clinical samples showed very good reproducibility (for the Ct values) when the positivity was quite high (Ct$\leq$to 36, status "positive-quantifiable"). For the Ct values>than 36 and up to 43, it may be considered that the target was present (positive), but the level of variation was too high to give a reliable quantification value.

Example 7

Linearity of the Quantification

The standard curve was conventionally generated, by PCR reaction, with the aid of 12 points ranging from $10^0$ to $10^5$ pfu which were assayed in duplicate. For each repetition, the amplification curves and PCR cycle values were very reproducible (see FIG. 1). Conversely, at the end point, the fluorescent signals were very variable (up to 10-fold), hence there was an advantage of analyzing the PCR products at the moment the signal appeared (PCR cycle: Ct), and not at the end point as in "conventional" PCR.

The standard curve obtained with these standard points is presented in FIG. 1. The correlation coefficient of 0.999 indicated excellent linearity. In the vast majority of cases, this coefficient was between 0.98 and 1. Manipulations using a wider standard range (0.5 to $10^6$ pfu) showed similar correlation coefficients (not shown), thus confirming the information from the device supplier which described quantification linearity over more than 6 logarithms.

The "Y-intercept" value represents the number of PCR cycles, deduced by the standard curve, to detect one pfu of Ad5CMVp53. Depending on the standard curves, this Ct value was between 35 and 39.

The value of the slope is linked to the yield of the PCR. It is recalled that for a PCR with 100% yield, this value should be −3.22. For the hexon PCR method in accordance with the invention, the value of the slope was between −3.4 to −3.9, which represents a mean yield of 90%.

Example 8

Quantification on Clinical Samples

The quantification examples obtained with the hexon PCR on the clinical samples (Table 7) were selected on two main criteria. The first criterion was that the sample was analyzed by two totally independent PCR extractions in series (see Table 6). The second criterion was that the PCR results have Ct values which were less than or equal to 36, which entirely corresponded to a quantifiable status for the sample.

Six clinical samples satisfy these two criteria (Table 7). The quantification results were very reproducible, and the level of variation rarely exceeded 2-fold for the same sample (Table 7). It is particularly advantageous to note, for urine No. 2403, that a difference of 3 Ct (in theory, this represents a factor of 8 for the quantification) between the two extractions has practically no effect on the quantification values determined by the hexon PCR. This example demonstrated the advantage of having the calibrators extracted in parallel, which made it possible to readjust the quantification as a function of the small fluctuations in the PCRs (slightly different detection threshold, slightly different extraction conditions, etc.).

TABLE No. 1

Optimized extraction techniques for the detection of adenoviruses originating from various types of sample.

| Type of sample | Kit used | Comments |
| --- | --- | --- |
| Adenovirus suspension or culture supernatant | High Pure RNA Isolation Kit (Boehringer/Roche) | 200 μl of extract solution. Without DNase step. 50 μl of sterile distilled water (elution). |
| Plasma | High Pure RNA Isolation Kit (BoehringerfRoche) | 200 μl of extract solution. Without DNase step. 50 μl of sterile distilled water (elution). |
| Urine | High Pure RNA Isolation Kit (Boehringer/Roche) | The urine was preheated for 10 minutes at 37° C. 200 μl of extract solution. Without DNase step. 50 μl of sterile distilled water (elution). |
| Oropharyngeal washes | High Pure RNA Isolation Kit (Boehringer/Roche) | 200 μl of extract solution. Without DNase step. 50 μl of sterile distilled water (elution). |
| Lymphocytes | High Pure PCR Template Preparation Kit (Boehringer/Roche) | The lymphocyte pellets ($\approx 2 \times 10^6$ cells) were resuspended beforehand in 200 μl of physiological saline (NaCl 9%). An additional centrifugation step was added before the final elution. |
| Seminal fluid | QlAmp Tissue Kit (Qiagen) | 100 μl of seminal fluid were lysed with 100 μl of SP buffer and 40 μl of proteinase K (for 1 h at 55° C.). The final elution was carried out with 60 μl of distilled water. |
| Biopsies (tumor or nontumor) | QlAmp Tissue Kit (Qiagen) | The lysis step was carried out overnight at 56° C. The final elution was carried out with 120 μl of distilled water. |
| Rectal swabs | High Pure RNA Isolation Kit (Boehringer/Roche) | The rectal swabs were resuspended in 5 ml of M4 medium (Micro Test Inc., USA). 200 μl of suspension were used for the extraction. Same comment as culture supernatants. |
| Feces | QlAmp Tissue Kit (Qiagen) | $\approx$100 mg of feces were resuspended in 1 ml of physiological saline. After centrifugation, the supernatant was filtered over 0.22 μm. 200 μl of suspension were used for the extraction. The final elution was carried out with 120 μl of distilled water. 10 μl diluted 10-fold were used for the PCR. |
| Ascites | High Pure RNA Isolation Kit (Boehringer/Roche) | 200 μl of extract solution. Without DNase step. 50 μl of sterile distilled water (elution). |

TABLE 2

Conditions for carrying out the reaction

| Reagents | Volumes | Final concentrations |
| --- | --- | --- |
| 10 X TaqMan ™ PCR buffer | 5 μl | 1X |
| 25 mM MgCl$_2$ | 10 μl | 5 mM |
| dNTPs (2 mM each dA, dG, dC, 4 mM dUTP) | 5 μl | (200 μM each dA, dG, dC, 400 μM dUTP) |
| HEX1 primer (50 pmol/μl) | 0.3 μl | 300 mM |
| HEX2 primer (50 pmol/μl) | 0.3 μl | 300 mM |
| HEX probe (10 pmol/μl) | 0.75 μl | 150 mM |
| AmpErase UNG (1 U/μl) | 0.5 μl | 0.5 unit |
| AmpliTaq Gold (5 U/μl) | 0.25 μl | 1.25 unit |
| Urine sample extract | 10 μl | |
| H$_2$0 | 17.9 μl | qs 50 μl |

TABLE 3

Delay in appearance of CPE (days), OD value by Elisa, Ct value (hexon PCR) and titer value by HPLC after inoculation, on A549 cells, of an MRC5-cell supernatant collected after infection with wild-type adenoviruses from the collection.

| Serotype | Group | CPE delay (days) | Elisa OD | Hexon PCR (Ct) | HPLC (particles/ml) |
| --- | --- | --- | --- | --- | --- |
| 1 | C | ≦3 | 1.385 | 8.5 | $1.2 \cdot 10^{10}$ |
| 2 | C | ≦3 | 1.120 | 8.1 | $2.3 \cdot 10^{10}$ |
| 3 | B1 | ≦3 | 0.732 | 8.5 | $4.8 \cdot 10^{10}$ |
| 4 | E | ≦3 | 1.222 | 9.0 | $3.9 \cdot 10^{10}$ |
| 5 | C | ≦3 | 1.211 | 8.5 | $6.6 \cdot 10^{10}$ |
| 6 | C | ≦3 | 1.428 | 8.1 | $6.6 \cdot 10^{10}$ |
| 7 | B1 | ≦3 | 1.344 | 9.0 | $4.4 \cdot 10^{10}$ |
| 11 | B2 | ≦3 | 1.648 | 8.5 | $3.8 \cdot 10^{10}$ |
| 12 | A | ≦3 | 2.759 | 21.6 | $<10^9$ |

TABLE 3-continued

Delay in appearance of CPE (days), OD value by Elisa, Ct value (hexon PCR) and titer value by HPLC after inoculation, on A549 cells, of an MRC5-cell supernatant collected after infection with wild-type adenoviruses from the collection.

| Serotype | Group | CPE delay (days) | Elisa OD | Hexon PCR (Ct) | HPLC (particles/ml) |
|---|---|---|---|---|---|
| 13 | D | ≦3 | 2.343 | 8.1 | $4.6 \times 10^{10}$ |
| 14 | B2 | ≦3 | 0.992 | 8.4 | $1.1 \times 10^{10}$ |
| 18 | A | 4 | >3 | 19 | $2.3 \times 10^{9}$ |
| 20 | D | ≦3 | 1.229 | 9.15 | $8.5 \times 10^{10}$ |
| 21 | B1 | ≦3 | 1.442 | 8.2 | $2.7 \times 10^{10}$ |
| 34 | B2 | ≦3 | 1.960 | 8.6 | $4.7 \times 10^{10}$ |
| 36 | D | ≦3 | 2.759 | 8.3 | $2.9 \times 10^{10}$ |
| 40 | F | 5 | 0.537 | 19.5 | $<10^{9}$ |

CPE: Cytopathic effect.
Elisa + if OD > 0.171.

TABLE 4

Kinetics of Ad2 culture on A549.
Delays in appearance of CPE (days), OD value by ELISA and Ct values of the hexon PCR.

| Nb of pfu/flask O.D. and Ct | D0 30/01 | D1 31/01 | D2 01/02 | D3 02/02 | D4 03/02 | D5 04/02 | D6 05/02 | D7 06/02 | D8 07/02 | D9 08/02 | D10 09/02 | D11 09/02 |
|---|---|---|---|---|---|---|---|---|---|---|---|---|
| $10^5$ | neg | neg | neg | neg | + | + | + | | | | | |
| OD | 0.072 | | 0.103 | | >3 | | 2.745 | | | | | |
| Ct1 | 31.91 | | | | | | | | | | | |
| Ct2 | 32.17 | | | | | | | | | | | |
| $10^4$ | neg | neg | neg | neg | +/− | + | + | | | | | |
| OD | 0.071 | | 0.187 | | 0.655 | | >3 | | | | | |
| Ct1 | 35.24 | | 31.65 | | 22.06 | | 14.77 | | | | | |
| Ct2 | 35.38 | | 31.81 | | 22.09 | | 14.76 | | | | | |
| $10^3$ | neg | neg | neg | neg | +/− | + | + | + | + | | | |
| OD | 0.073 | | 0.134 | | 0.116 | | >3 | | 2.446 | | | |
| Ct1 | 37.21 | | 40.96 | | 25.77 | | 15.74 | | 14.62 | | | |
| Ct2 | 37.67 | | 40.49 | | 25.70 | | 15.76 | | 14.65 | | | |
| $10^2$ | neg | neg | neg | neg | neg | neg | + | + | + | | | |
| OD | ND | | 0.082 | | ND | | 1.107 | | >3 | | | |
| Ct1 | 39.44 | | 39.39 | | 28.84 | | 19.59 | | 14.91 | | | |
| Ct2 | 40.52 | | 41.15 | | 29.04 | | 19.64 | | 15.15 | | | |
| 10 | neg | neg | neg | neg | neg | neg | neg | + | + | + | + | |
| OD | ND | | ND | | 0.086 | | 0.101 | | 1.716 | | >3 | |
| Ct1 | 42.52 | | 38.44 | | 37.97 | | 25.41 | | 18.08 | | 14.98 | |
| Ct2 | 40.95 | | 39.55 | | 37.25 | | 25.36 | | 18.14 | | 14.96 | |
| 1 | neg | neg | neg | neg | neg | neg | neg | neg | neg | neg | neg | neg |
| OD | ND | | | | ND | | 0.081 | | 0.091 | | 0.310 | |
| Ct1 | 35.34 | | | | 35.57 | | 32.13 | | | | 28.71 | |
| Ct2 | 35.19 | | | | 35.45 | | 31.88 | | | | 28.75 | |
| C | neg | neg | neg | neg | neg | neg | neg | neg | neg | neg | neg | neg |
| OD | 0.073 | | 0.082 | | ND | | 0.288 | | 0.117 | | 0.159 | |
| Ct1 | 37.61 | | | | | | | | | | 31.25 | |
| Ct2 | 37.77 | | | | | | | | | | 31.25 | |

1st line CPE: Cytopathic effect
2nd line Elisa (Elisa+ if OD > 0.171)
3rd and 4th lines hexon PCR Ct1 and Ct2
ND: Not Done; C: control

TABLE 5

Ct values obtained with 1 pfu of Ad5CMVp53 in the PCR reaction (101 assays)

| Assay No. | No. of series in the assay | Ct1 | Ct2 |
|---|---|---|---|
| P199812702 | 41 | 35.8 | 36.3 |
| P199814602 | 41 | 36.8 | 36.9 |
| P199814902 | 30 | 41.2 | 39.5 |
| P199815602 | 41 | 37.3 | 39.1 |
| P199817403 | 35 | 39.4 | 38.1 |
| P199817702 | 34 | 37.2 | 36.8 |
| P199818802 | 41 | 37.1 | 37.4 |
| P199819802 | 41 | 35.7 | 37.5 |
| P199820302 | 41 | 37.2 | 36.5 |
| P199820502 | 41 | 38.6 | 40.3 |
| P199821602 | 41 | 38.9 | 38.3 |
| P199822302 | 41 | 39.6 | 38.3 |
| P199823102 | 41 | 43.6 | 40 |
| P199823702 | 40 | 41.7 | 39.3 |
| P199824002 | 41 | 36.4 | 37.8 |
| P199824702 | 41 | 40.8 | 38.1 |
| P199825103 | 41 | 37.4 | 39.1 |

TABLE 5-continued

Ct values obtained with 1 pfu of Ad5CMVp53 in the PCR reaction (101 assays)

| Assay No. | No. of series in the assay | Ct1 | Ct2 |
|---|---|---|---|
| P199826101 | 41 | 36.8 | 37 |
| P199826501 | 41 | NEG[a] | 39.8 |
| P199826801 | 41 | 36.6 | 37.1 |
| P199828201 | 41 | 40 | 40.8 |
| P199829302 | 41 | 36.4 | 36.9 |
| P199829601 | 41 | 36.2 | 36.8 |
| P199830301 | 41 | 40.9 | NEG |
| P199830701 | 41 | 39.9 | 39.4 |
| P199831001 | 41 | 36.8 | 37.3 |
| P199831401 | 41 | NEG | 40.5 |
| P199832101 | 39 | 39.4 | 40 |
| P199833501 | 41 | 44.4 | 39.6 |
| P199833801 | 41 | 37.9 | 38.8 |
| P199834201 | 41 | NEG | NEG |
| P199834901 | 41 | 38.2 | 38.2 |
| P199835101 | 41 | 38.1 | 38 |
| P199835601 | 41 | 38.5 | 40.7 |
| P199836301 | 41 | 41.1 | NEG |
| P199900501 | 41 | 38.5 | 38 |
| P199900801 | 41 | 37.8 | 37.7 |
| P199901401 | 41 | 39 | 40.3 |
| P199902201 | 41 | 39.9 | 38.4 |
| P199902901 | 41 | 37.5 | 37.7 |
| P199906101 | 41 | 38.6 | 37.2 |
| P199906301 | 41 | 37.9 | 37.2 |
| P199906401 | 41 | 41 | 41.3 |
| P199906901 | 34 | 37.9 | 38.2 |
| P199907001 | 40 | 37.5 | 37.3 |
| P199907101 | 41 | 37.2 | 38.6 |
| P199907701 | 41 | 37.8 | 36.9 |
| P199907801 | 41 | 39.3 | 41.2 |
| P199908201 | 41 | 36.8 | 37.4 |
| P199908301 | 41 | 38.7 | 38.1 |
| P199908401 | 41 | 37.9 | 38 |
| P199908901 | 41 | NEG | NEG |
| P199909101 | 41 | 37.6 | 36.8 |
| P199909801 | 41 | 39.2 | 38 |
| P199909901 | 41 | 37.5 | 38.1 |
| P199910401 | 41 | 39.2 | 38.5 |
| P199911101 | 41 | 35.5 | 35.5 |
| P199911701 | 41 | 37.9 | 36.4 |
| P199911801 | 33 | 34.5 | 35 |
| P199912501 | 41 | 36.3 | 36.4 |
| P199913101 | 41 | 36.8 | 37.1 |
| P199914601 | 41 | 35.4 | 36.2 |
| P199914801 | 41 | 35.4 | 35.2 |
| P199915401 | 40 | 38 | ND[b] |
| P199915501 | 39 | 37 | 36.2 |
| P199916001 | 41 | 36.2 | 35.7 |
| P199916101 | 41 | 35.7 | 36.5 |
| P199916201 | 25 | 36.3 | 35.4 |
| P199917301 | 41 | 37.1 | 36 |
| P199917501 | 41 | 37.3 | 36.5 |
| P199918001 | 41 | 37.3 | 37.1 |
| P199918201 | 41 | 36.8 | 36.7 |
| P199919001 | 41 | 35.3 | 35.2 |
| P199919703 | 41 | 34.7 | 34.3 |
| P199920101 | 41 | 36.1 | 35 |
| P199920201 | 41 | 34 | 34.9 |
| P199920801 | 32 | 39.6 | 36 |
| P199921501 | 41 | 36.5 | 35.5 |
| P199922201 | 41 | 34.4 | 34.4 |
| P199922401 | 29 | 35.5 | 36.3 |
| P199924301 | 41 | 34.9 | 34.7 |
| P199924501 | 22 | 36.6 | 35.6 |
| P199925001 | 41 | 34.5 | 35 |
| P199925201 | 32 | 35.5 | 36.1 |
| P199925901 | 41 | 35.9 | 36.2 |
| P199926401 | 36 | 36.7 | 35.7 |
| P199926601 | 25 | 36.7 | 36.3 |
| P199927801 | 29 | 35.6 | 35.9 |
| P199927901 | 10 | 34.6 | 34 |
| P199928101 | 31 | 35.2 | 34.7 |
| P199928501 | 41 | 36.1 | 35.9 |
| P199929301 | 32 | 34.7 | 34.4 |
| P199929901 | 39 | 35.1 | 35.1 |
| P199930101 | 36 | 35.3 | 35.5 |
| P199932001 | 41 | 36.2 | 36.4 |
| P199932801 | 40 | 35.6 | 35.3 |
| P199933001 | 33 | 35.5 | 36.2 |
| P199933501 | 19 | 36 | 35.9 |
| P199934401 | 25 | 36.9 | 37 |

[a]NEG: Negative, Ct = 50.
[b]ND: Not Done

TABLE 6

Results of the hexon PCR with two collections of clinical samples (plasma and urine) which have had two or three independent extractions.

| Series No. | Type of sample | Hexon PCR (Ct) | | | | | |
|---|---|---|---|---|---|---|---|
| | | Ext 1[a] | | Ext 2 | | Ext 3 | |
| | | Ct1[d] | Ct2[d] | Ct1[d] | Ct2[d] | Ct1[d] | Ct2[d] |
| 1518 | Plasma | 35.37 | 35.29 | 37.28 | 37.46 | NA[b] | NA |
| 3289 | | 38.31 | 36.76 | 36.95 | 37.57 | NA | NA |
| 3579 | | 35.81 | 36.24 | 36.35 | 36.22 | 44.60 | 35.98 |
| 4823 | | 36.00 | 35.74 | 35.07 | 35.25 | NA | NA |
| 5593 | | 37.06 | 36.88 | 35.46 | 34.79 | NA | NA |
| 5686 | | 36.87 | 37.92 | 35.68 | 36.12 | NA | NA |
| 5870 | | 36.81 | 37.50 | 35.73 | 36.01 | NA | NA |

TABLE 6-continued

Results of the hexon PCR with two collections of clinical samples (plasma and urine) which have had two or three independent extractions.

| | | Hexon PCR (Ct) | | | | | |
|---|---|---|---|---|---|---|---|
| | | Ext 1[a] | | Ext 2 | | Ext 3 | |
| Series No. | Type of sample | Ct1[d] | Ct2[d] | Ct1[d] | Ct2[d] | Ct1[d] | Ct2[d] |
| 2025 | Urine | 33.72 | 33.32 | 33.60 | 33.03 | NA | NA |
| 2029 | | 43.02 | 50.00 | 40.59 | 44.82 | 43.05 | 41.21 |
| 2041 | | 39.00 | 40.46 | 38.24 | 39.30 | NA | NA |
| 2045 | | 37.85 | 38.45 | 38.50 | 36.36 | NA | NA |
| 2049 | | 35.75 | 34.75 | 35.74 | 34.66 | 36.08 | 36.14 |
| 2097 | | 37.50 | 36.13 | 37.03 | 35.63 | NA | NA |
| 2384 | | 37.40 | 35.80 | 34.58 | 34.55 | NA | NA |
| 2392 | | 40.95 | 38.72 | 38.08 | 40.29 | NA | NA |
| 2397 | | 38.27 | 36.08 | 36.02 | 36.36 | NA | NA |
| 2400 | | 35.56 | 35.45 | 36.63 | 35.45 | NA | NA |
| 2403 | | 32.62 | 32.04 | 29.36 | 29.41 | NA | NA |
| 2406 | | 35.36 | 34.42 | 34.08 | 33.37 | NA | NA |
| 2626 | | 50.00[c] | 40.13 | 50.00 | 42.67 | NA | NA |
| 3277 | | 38.38 | 38.22 | 39.52 | 41.02 | NA | NA |
| 3736 | | 40.05 | 41.80 | 45.08 | 43.52 | NA | NA |
| 3763 | | 38.48 | 40.63 | 50.00 | 43.68 | NA | NA |
| 3765 | | 40.40 | 41.84 | 43.41 | 43.30 | NA | NA |
| 5399 | | 50.00 | 41.29 | 43.29 | 43.73 | NA | NA |
| 5400 | | 37.60 | 37.18 | 39.96 | 38.64 | NA | NA |

[a]Ext: Extraction. The figure indicates the number of extractions carried out on the same sample.
[b]NA: Not Applicable;
[c]Ct = 50: negative PCR.
[d]Each extract was assayed in 2 PCR reactions, Ct 1 for PCR assay 1 and Ct 2 for PCR assay 2.

TABLE 7

Quantification using the hexon PCR with quantifiable clinical samples.

| | | Extraction No. 1 | | Extraction No. 2 | |
|---|---|---|---|---|---|
| Series No. | Type of sample | Mean of Ct[a] | Quantification (Ad5CMVp53pfu equivalent/ml)[b] | Mean of Ct | Quantification (Ad5CMVp53pfu equivalent/ml) |
| 4823 | Plasma | 35.87 | $1.1 \times 10^2$ | 35.16 | $1.8 \times 10^2$ |
| 2925 | Urine | 35.52 | $2.6 \times 10^3$ | 33.31 | $2.8 \times 10^3$ |
| 2049 | | 35.25 | $8.5 \times 10^2$ | 35.20 | $8.4 \times 10^2$ |
| 2400 | | 35.50 | $6.5 \times 10^2$ | 36.04 | $7.4 \times 10^2$ |
| 2403 | | 32.33 | $2.3 \times 10^4$ | 29.38 | $3.8 \times 10^4$ |
| 2406 | | 34.89 | $5.1 \times 10^3$ | 33.72 | $2.2 \times 10^3$ |

[a]The mean was calculated from the Ct values indicated in Table 6.
[b]The standard used has a known number of Ad5CMVp53pfu. This quantification is given by milliliter of starting clinical samples.

We claim:

1. A method for detecting adenovirus nucleic acid in a biological sample, comprising:
   producing an amplification product by amplifying an adenovirus nucleotide sequence by real-time PCR using degenerate sense primers and degenerate antisense primers, wherein said primers are chosen from oligonucleotides that hybridize, under conditions suitable for a polymerase chain reaction, with a sequence between nucleotides 21000 and 22000 of type 5 adenovirus sequence; and
   detecting said amplification product by using a nondegenerate probe comprising an oligonucleotide that hybridizes, under conditions suitable for a polymerase chain reaction, with a sequence between nucleotides 21000 and 22000 of type 5 adenovirus sequence.

2. The method according to claim 1, wherein at least one of said primers is an oligonucleotide comprising at least 10 consecutive nucleotides of SEQ ID No. 1 or a sequence that hybridizes, under conditions suitable for a polymerase chain reaction, with:
   5'-YCC CAT GGA YGA GCC CAC MCT-3'(SEQ ID No. 5) wherein each Y, which may be the same or different, is independently chosen from C and T, and M is chosen from A and C.

3. The method according to claim 2, further comprising a primer comprising a sequence complementary to an oligonucleotide according to claim 2.

4. The method according to claim 1, wherein at least one of said primers is an oligonucleotide comprising at least 10 consecutive nucleotides of SEQ ID No. 2 or a sequence that hybridizes, under conditions suitable for a polymerase chain reaction, with:
   5'-GAG AAS GGB GTG CGC AGG TAS AC-3'(SEQ ID No. 6) wherein each S, which may be the same or different, is independently chosen from G and C, and B is chosen from C, G and T.

5. The method according to claim 4, further comprising at least one primer comprising a sequence complementary to an oligonucleotide, wherein the oligonucleotide comprises at least 10 consecutive nucleotides of SEQ ID No. 2 or a sequence having at least 80% sequence homology with sequence:
   5'-GAG AAS GGB GTG CGC AGG TAS AC-3'(SEQ ID No. 6) wherein each S, which may be the same or different, is independently chosen from G and C. and B is chosen from C, G and T.

6. The method according to claim 1, wherein said probe comprises an oligonucleotide comprising at least 10 consecutive nucleotides of SEQ ID No. 3 or a sequence that hybridizes, under conditions suitable for a polymerase chain reaction, with:
   5'-CAC GAG CCA GAG CGC GGC GTC ATC GA-3' (SEQ ID No. 3); or a sequence complementary thereof.

7. The method according to claim 1, wherein said probe comprises from 20 to 35 nucleotides.

8. The method according to claim 1, wherein said probe comprises a revealing molecule or a revealing system of molecules.

9. The method according to claim 1, wherein said probe comprises:

5'-FAM-CAC CAG CCA CAC CTC GGC ATC GA-TAMRA 3'.

10. The method according to claim 1, comprising at least one repetition of a cycle comprising:
    separation of the strands to be amplified by heating the DNA extracted from the sample,
    hybridization of the probe,
    hybridization with primers as defined above, and
    elongation with a polymerase.

11. The method according to claim 1, wherein at least one of said degenerate sense primers, degenerate antisense primers, or nondegenerate probe comprises from 20 to 35 nucleotides.

12. The method according to claim 11, wherein at least two of said degenerate sense primers, degenerate antisense primers, or nondegenerate probe each comprise from 20 to 35 nucleotides.

13. The method according to claim 1, wherein said adenoviral nucleic acid is extracted from said biological sample before amplification.

14. An oligonucleotide comprising at least 10 consecutive nucleotides of SEQ ID No. 1 or a sequence that hybridizes, under conditions suitable for a polymerase chain reaction, with:
    5'-YCC CAT GGA YGA GOC GAG MCT-3'(SEQ ID No. 5),
    wherein each Y, which may be the same or different, is independently chosen from C and T, and M is chosen from A and C; or a sequence complementary thereof.

15. The oligonucleotide according to claim 14, comprising from 15 to 30 nucleotides.

16. A HEX1 primer comprising at least two oligonucleotides according to claim 14.

17. The HEX1 primer according to claim 16, comprising at least three oligonucleotides according to claim 14.

18. An oligonucleotide, comprising at least 10 consecutive nucleotides of SEQ ID No. 2 or a sequence that hybridizes, under conditions suitable for a polymerase chain reaction, with:
    5'-GAG AAS GGB GTG CGC AGG TAS AC-3'(SEQ ID No. 6)
    wherein each S, which may be the same or different, is independently chosen from G and C, and B is chosen from C, G and T; or a sequence complementary thereof.

19. The oligonucleotide according to claim 18, comprising from 15 to 30 nucleotides.

20. A HEX2 primer, comprising at least two oligonucleotides according to claim 18.

21. The HEX2 primer according to claim 20, comprising at least three oligonucleotides according to claim 18.

22. An oligonucleotide, comprising at least 10 consecutive nucleotides of SEQ ID No. 3 or a sequence that hybridizes, under conditions suitable for a polymerase chain reaction, with:
    5'-CAC GAG CCA GAG CGC GGC GTC ATC GA-3' (SEQ ID No. 3); or a sequence complementary thereof.

23. The oligonucleotide according to claim 22, comprising from 20 to 35 nucleotides.

24. A HEX probe, comprising at least one oligonucleotide according to claim 22.

25. The HEX probe according to claim 24, comprising a revealing molecule or a revealing system of molecules.

26. The HEX probe according to claim 25, comprising:

5'FAM-CAC CAG CCA CAC CGC GGC GTC ATC GA-TAMRA 3'.

27. A composition comprising degenerate sense primers, degenerate antisense primers and a nondegenerate probe, wherein said primers and probe are chosen from oligonucleotides that hybridize, under conditions suitable for a polymerase chain reaction, with a sequence between nucleotides 21000 and 22000 of type 5 adenovirus sequence, or a complementary sequence thereof.

28. The composition according to claim 27, wherein at least one of said primers comprise an oligonucleotide comprising at least 10 consecutive nucleotides of SEQ ID No. 1 or a sequence that hybridizes, under conditions suitable for a polymerase chain reaction, with:

5'-YCC CAT GGA YGA GCC CAC MCT-3'(SEQ ID No. 5);

wherein each Y, which may be the same or different, is independently chosen from C and T, and M is chosen from A and C; or a sequence complementary thereof.

29. The composition according to claim 28, wherein said oligonucleotide comprises from 15 to 30 nucleotides.

30. The composition according to claim 27, comprising a HEX1 primer comprising at least two said oligonucleotides according to claim 28.

31. The composition according to claim 30, wherein said HEX1 primer comprises at least three said oligonucleotides according to claim 28.

32. The composition according to claim 27, wherein at least one of said primers comprise an oligonucleotide comprising at least 10 consecutive nucleotides of SEQ ID No. 2 or a sequence that hybridizes, under conditions suitable for a polymerase chain reaction, with:

5'-GAG AAS GGB GTG GGC AGG TAS AG-3'(SEQ ID No. 6)

wherein each S, which may be the same or different, is independently chosen from G and C, and B is chosen from C, G and T;

or a sequence complementary thereof.

33. The composition according to claim 32, wherein said oligonucleotide comprises from 15 to 30 nucleotides.

34. The composition according to claim 27, comprising a HEX2 primer comprising at least two said oligonucleotides according to claim 32.

35. The composition according to claim 34, wherein said HEX2 primer comprises at least three said oligonucleotides according to claim 32.

36. The composition according to claim 27, comprising an oligonucleotide comprising at least 10 consecutive nucleotides of SEQ ID No. 3 or a sequence that hybridizes, under conditions suitable for a polymerase chain reaction, with:

5'-CAC CAG CCA GAG CGC GGC GTC ATC GA-3' (SEQ ID No. 3); or a sequence complementary thereof.

37. The composition according to claim 36, wherein said oligonucleotide comprises from 20 to 30 nucleotides.

38. The composition according to claim 36, further comprising an oligonucleotide comprising a sequence complementary to said oligonucleotide sequence according to claim 36.

39. The composition according to claim 27, comprising a HEX probe comprising at least one said oligonucleotides according to claim 36.

40. The composition according to claim 39, wherein said HEX probe comprises a revealing molecule or a revealing system of molecules.

41. The composition according to claim 40, wherein said HEX probe comprises the following molecule:

5'-FAM-CAC CAG CCA CAC CGC GGC GTC ATC GA-TAMRA 3'.

42. A kit comprising reagents for real-time PeR-type amplification reaction for detecting adenoviruses, comprising degenerate sense primers, degenerate antisense primers and a nondegenerate probe, wherein said primers and probe are chosen from oligonucleotides that hybridize, under conditions suitable for a polymerase chain reaction, with a sequence between nucleotides 21000 and 22000 of type 5 adenovirus sequence, or a complementary sequence thereof.

43. The kit according to claim 42, wherein at least one said primers is chosen from:

an oligonucleotide comprising at least 10 consecutive nucleotides comprising a sequence of SEQ ID No. 1 or a sequence that hybridizes, under conditions suitable for a polymerase chain reaction, with:
5'-YCC CAT GGA YGA GCC GAG MCT-3'(SEQ ID No. 5) wherein each Y, which may be the same or different, is independently chosen from C and T, and M is chosen from A and C;

an oligonucleotide comprising at least 10 consecutive nucleotides comprising a sequence of SEQ ID No. 2 or a sequence that hybridizes, under conditions suitable for a polymerase chain reaction, with:
5'-GAG AAS GGB GTG CGC AGG TAS AC-3'(SEQ ID No. 6) wherein each S, which may be the same or different, is independently chosen from G and C, and B is chosen from C, G and T; and a sequence complementary thereof.

44. The kit according to claim 42, wherein said probe is chosen from:

an oligonucleotide comprising at least 10 consecutive nucleotides of SEQ ID No. 3;

a sequence that hybridizes, under conditions suitable for a polymerase chain reaction, with:
5'-CAC GAG CCA GAG CGC GGG GTG ATC GA-3' (SEQ ID No. 3); and a sequence complementary thereof.

45. A kit according to claim 44, wherein said probe is

5'-FAM-CAC CAG CCA CAC CGC GGC GTC ATC GA-TAMRA 3'.

46. A method for diagnosing the serotype of at least one type of adenovirus present in a sample, comprising:

producing an amplification product by amplifying an adenovirus nucleotide sequence by real-time PCR using degenerate sense primers and degenerate antisense primers, wherein said primers are chosen from oligonucleotides that hybridize, under conditions suitable for a polymerase chain reaction, with a sequence between nucleotides 21000 and 22000 of type 5 adenovirus sequence; and detecting said amplification product by using a nondegenerate probe comprising an oligonucleotide that hybridizes, under conditions suitable for a polymerase chain reaction, with a sequence between nucleotides 21000 and 22000 of type 5 adenovirus sequence; and sequencing the amplification product obtained.

47. A method for selecting adenoviruses which are useful as vector candidates, comprising:

producing an amplification product by amplifying an adenovirus nucleotide sequence by real-time PCR using degenerate sense primers and degenerate antisense primers, wherein said primers are chosen from oligonucleotides that hybridize, under conditions suitable for a polymerase chain reaction, with a sequence between nucleotides 21000 and 22000 of type 5 adenovirus sequence; and detecting said amplification product by using a nondegenerate probe comprising an oligonucleotide that hybridizes, under conditions suitable for a polymerase chain reaction, with a sequence between nucleotides 21000 and 22000 of type 5 adenovirus sequence;

48. A method for quantifying adenovirus nucleic acid in a biological sample, comprising:

producing an amplification product by amplifying an adenovirus nucleotide sequence by real-time PCR using degenerate sense primers and degenerate antisense primers, wherein said primers are chosen from oligonucleotides that hybridize, under conditions suitable for a polymerase chain reaction, with a sequence between nucleotides 21000 and 22000 of type 5 adenovirus sequence; and detecting said amplification product by using a nondegenerate probe comprising an oligonucleotide that hybridizes, under conditions suitable for a polymerase chain reaction, with a sequence between nucleotides 21000 and 22000 of type 5 adenovirus sequence; and quantifying said amplification product in said biological sample by measuring a detection signal from said probe and comparing said detection signal to a second probe detection signal from a quantification standard, wherein said quantification standard comprises a degenerate sense probe and a nucleic acid standard.

49. The method according to claim 48, wherein said adenoviral nucleic acid is extracted from said biological sample before amplification.

50. The method according to claim 49, wherein said quantification standard is extracted in parallel with said biological sample.

51. The method according to claim 48, wherein said nucleic acid standard comprises a purified and titered adenovirus solution.

52. The method according to claim 50, wherein said detection signal from said probe is further compared to a third probe detection signal from a nucleic acid calibrator extracted in parallel to said biological sample, wherein said nucleic acid calibrator comprises a degenerate sense probe and a nucleic acid calibrator.

53. The method according to claim 52, wherein said calibrator comprises a known amount of adenovirus and a known amount of a medium similar to the biological sample.

* * * * *

UNITED STATES PATENT AND TRADEMARK OFFICE
CERTIFICATE OF CORRECTION

PATENT NO. : 6,541,246 B2  Page 1 of 1
DATED : April 1, 2003
INVENTOR(S) : Vidaud et al.

It is certified that error appears in the above-identified patent and that said Letters Patent is hereby corrected as shown below:

Column 23,
Line 46, "and C." should read -- and C, --.
Line 53, "GAG CCA GAG" should read -- CAG CCA CAC --.
Line 63, "5'-FAM-CAC CAG CCA CAC CTC GGC ATC" should read
-- 5'FAM-CAC CAG CCA CAC CGC GGC GTC ATC --.

Column 24,
Line 19, "GOC GAG" should read -- GCC CAC --.
Line 49, "GAG CCA GAG" should read -- CAG CCA CAC --.

Column 25,
Line 24, "GGC" should read -- CGC --.
Line 43, "GAG" should read -- CAC --.
Line 60, "5'-FAM-CAC" should read -- 5'FAM-CAC --.
Line 62, "PeR-type" should read -- PCR-type --.

Column 26,
Line 9, "GAG" should read -- CAC --.
Line 29, "GAG CCA GAG CGC GGG GTG" should read -- CAG CCA CAC CGC GGC GTC --.
Line 34, "5'-FAM-CAC" should read -- 5'FAM-CAC --.
Line 67, "sequence;" should read -- sequence. --.

Signed and Sealed this

Ninth Day of March, 2004

JON W. DUDAS
*Acting Director of the United States Patent and Trademark Office*